United States Patent [19]

Turner

[11] Patent Number: 5,288,642
[45] Date of Patent: Feb. 22, 1994

[54] SHELF-STABLE MILK CALIBRATION STANDARDS

[75] Inventor: Jeffrey D. Turner, Hudson, Canada

[73] Assignee: Flockton Analytical Management Inc., Cornwall, Canada

[21] Appl. No.: 987,825

[22] Filed: Dec. 9, 1992

[51] Int. Cl.$^5$ ............... G01N 31/00; G01N 31/22; G01N 33/04
[52] U.S. Cl. ............... 436/8; 436/10; 436/19; 252/408.1
[58] Field of Search ............... 436/8, 10, 19; 252/408.1

[56] References Cited

U.S. PATENT DOCUMENTS

| | | | |
|---|---|---|---|
| 4,174,682 | 12/1987 | Schwartz | 436/10 |
| 4,609,689 | 9/1986 | Schwartz et al. | 523/202 |
| 4,767,206 | 8/1988 | Schwartz | 356/73 |
| 4,774,189 | 9/1988 | Schwartz | 436/10 |
| 4,857,451 | 8/1989 | Schwartz | 435/7 |
| 4,867,908 | 9/1989 | Recktenwald et al. | 252/408.1 |
| 4,868,126 | 9/1989 | Schwartz | 436/10 |
| 5,073,497 | 12/1991 | Schwartz | 436/8 |
| 5,073,498 | 12/1991 | Schwartz | 436/8 |

OTHER PUBLICATIONS

The Merck Index, Tenth Edition, 1983, p. 260.

Primary Examiner—James C. Housel
Assistant Examiner—Rachel Freed
Attorney, Agent, or Firm—Swabey Ogilvy Renault

[57] ABSTRACT

A calibration standard for calibrating machines which count the somatic cells in a milk sample, comprises an aqueous dispersion of microbeads bearing a fluorescent dye, a suspending agent, and an electrolyte; the dye has an excitation wavelength below 580 nm and a fluorescence emission wavelength in the range of 550 to 660 nm, with the excitation wavelength being at least 10 nm below the emission wavelength; the microbeads are present in a predetermined number per unit volume of dispersion; typically the standard contains $1 \times 10^5$ to $9 \times 10^5$ beads/ml.

8 Claims, 1 Drawing Sheet

SHELF-STABLE MILK CALIBRATION STANDARDS

BACKGROUND OF THE INVENTION i) Field of the Invention

This invention relates to a calibration standard for calibrating a machine employed in the determination of the somatic cell count of milk, and more especially a shelf-stable standard; the invention also relates to the use of the calibration standard in the determination of the somatic cell count of milk samples.

ii) Description of Prior Art

The production of high quality milk is an objective of the dairy industry. By providing special care and close monitoring of the health status of their dairy cattle, farmers hope to reduce losses due to mastitis. Most commonly, subclinical mastitis caused by bacterial infections leads to a decrease in milk production. Early detection of such infections, is the cornerstone of udder health and has been shown to improve milk production and reduce production costs.

Mastitis occurs when bacteria enter through the streak canal of the teat and move into the udder where they multiply. The onset of mastitis stimulates the cows immune system, with the response of leucocytes migrating into the milk. Leucocytes, also referred to as somatic cells when found in milk, increase in number in milk in relation to the severity of mammary infection. Therefore the ability to accurately enumerate somatic cells in milk serves as an important method to detect mastitis before severe damage can occur to the cow's udder. The methods used to detect somatic cells in milk range from cow side testing to automated cell counters. However, the direct enumeration of somatic cells is usually employed by farm managers in milk recording programs or the dairy food industry for quality control purpose.

One of the services that Dairy Herd Analysis Centers provide to dairy farmers of the world is somatic cell counting of milk for the early detection of mastitis. There are two predominant types of machines which serve this function, the Coulter counter and the Fossomatic type cell counter, and the more recent Bentley Soma, referred to above.

Automated cell counting systems measure fluorescent light emission that occurs as stained somatic cells are observed by an electronic micro-optical system or when unstained somatic cells move through an electromagnetic field and are counted.

Typical of commercial machines which measure fluorescent light emission are the Fossomatic (Trade Mark) and Bentley Soma (Trade Mark) machines. Typical of machines which measure cells moving through an electromagnetic field is a Coulter (Trade Mark) counter.

Direct microscopic count can be achieved by examination of milk somatic cells under a microscope, the cells being fixed and stained to facilitate counting.

When employing these machines it is necessary to employ a calibration standard, and the standards widely used are cells from milk. The cell count of these standards is achieved by the method of direct microscopic determination, which counting method is tedious, time consuming and costly. Additionally, calibration standards derived from milk are of low stability and have a short shelf life.

Calibrating standards based on microbeads have been proposed for the alignment and calibration of flow cytometers and fluorescent microscopes. Representative Patents in this field are U.S. Pat. Nos. 4,867,908; 4,857,451; 5,073,497; 4,609,689; 5,073,489; 4,774,189; 4,714,682 and 4,868,126. These calibrating standards are employed under flow conditions which are such that the beads remain in suspension. These calibrating standards are not suitable as milk calibration standards employing the commercially available machines described hereinbefore. In particular the commercially available machines do no employ the standard under flow conditions, and under static or non-flow conditions the microbeads in these calibrating standards for flow cytometers and fluorescent microscopes, settle from suspension and distort the results received. Surprisingly, agitation to resuspend the microbeads does not overcome the problem. Although available commercial machines, such as the Fossomatic and Bentley machines have some agitating capability it does not appear to be effective in re-suspending beads.

SUMMARY OF THE INVENTION

It is an object of this invention to provide a shelf-stable milk calibration standard.

It is a further object of this invention to provide an improved method of determining the somatic cell count of milk.

In accordance with one aspect of the invention there is provided a shelf-stable milk calibration standard comprising an aqueous dispersion of microbeads bearing a fluorescent dye, a suspending agent effective to maintain said microbeads in a dispersed state in said dispersion and an electrolyte in an amount to render the dispersion electrically conductive, said dye having an excitation wavelength below 580 nm, and having a fluorescence emission wavelength in the range of 550 to 660 nm, with said excitation wave length being at least 10 nm below said emission wavelength, and said microbeads being present in a predetermined number per unit volume of the dispersion.

In accordance with another aspect of the invention there is provided an improved method of determining the somatic cell count of milk, in which a sample of the milk is mixed with a dye which reacts with the somatic cells to produce fluorescence, and the fluorescence is detected and transformed to electrical pulses which are counted and evaluated based on a calibration standard of predetermined characteristics; the improvement comprises employing as the calibration standard, the shelf-stable milk calibration standard of the invention.

DESCRIPTION OF PREFERRED EMBODIMENTS a) Calibration Standards i) Dispersion

The calibration standard of the invention is an aqueous dispersion of microbeads bearing a fluorescent dye, the dispersion contains an emulsifying agent and an electrolyte. It is appropriate to maintain the pH of the dispersion close to neutral and in particular, at a pH of 6 to 8; for this purpose the dispersion suitably contains a buffer. A suitable buffer solution comprises potassium hydrogen phthalate and potassium hydroxide in deionized water.

ii) Microbeads

The microbeads are, in particular, derived from a synthetic water-insoluble homopolymer or copolymer. Especially preferred microbeads are polystyrene microbeads, however, any water-insoluble homopolymer or copolymer can be employed which is capable of forming microbeads and of forming a support for a fluorescent dye, while being otherwise inert, and non-interfering in the calibration procedure.

The homopolymer or copolymer must have reactive groups capable of binding the dye directly to the microbeads, or capable of binding the dye to the microbeads indirectly through a linking unit. In either case the binding must be such that it does not interfere with the fluorescing characteristics of the dye such that it would be suitable for the purposes of the invention; additionally the binding must be such that the dye remains bound to the bead and does not leach or otherwise separate from the bead with the passage of time.

The dye may be any fluorescent dye capable of being bound to the microbeads, without interference with the fluorescing characteristics, which has an extinction wavelength at least 10 nm and preferably at least 20 nm below the emission wavelength, and which has an excitation wavelength below 580 nm, and a fluorescence emission wavelength in the range of 550 to 660 nm.

The dye widely used in the milk samples under investigation is ethidium bromide; this dye interacts with DNA present in the nucleus of the somatic cells of the milk to produce a strong fluorescence. It is thus especially preferred to employ in the dispersion a dye which will mimic the fluorescing characteristics of ethidium bromide in its interaction with DNA. Ethidium bromide itself does not fluoresce in the absence of DNA and thus is not useful in the dispersions of the invention.

Especially suitable microbeads bearing a fluorescent dye, in accordance with the invention, are polystyrene microbeads having a diameter of about 6 microns. These dye-bearing microbeads are available under the Trade Mark Fluoresbrite polychromatic, as a dispersion in sterile distilled water from Polysciences Inc. of Warrington, Pa., U.S.A.; the dye is PC red a dye having the same spectral characteristics as the phycoerythin class of phycobiliproteins.

The microbeads suitably have a diameter in the range of 0.5 to 10 microns, preferably 4 to 8 microns and most preferably about 6 microns, this being a diameter which simulates that of the nuclei of somatic cells in milk. The size of individual microbeads in a population of microbeads is not critical, but they should suitably all be of a size falling within the above ranges. Thus the population of microbeads in the dispersion may comprise beads of different diameters within the range of 0.5 to 10 microns. This is in contrast to some prior techniques where uniformity of bead size is very important; for example, the Coulter counter is very sensitive to variations in bead size in the population of beads in the calibration standard.

The dispersion suitably contains $5 \times 10^4$ to $1 \times 10^6$ beads/ml of dispersion, and in particular will contain a predetermined or known number of microbeads per unit volume of the dispersion. Typically the dispersion contains $1 \times 10^5$ to $9 \times 10^5$ beads/ml.

The dispersion suitably includes a small amount of a surfactant or detergent to prevent agglomeration of the microbeads. In this way a dispersion of discrete microbeads is maintained, simulating the discrete somatic cells in milk. In the absence of a surfactant or detergent there is a tendency for agglomeration or clustering of the microbeads which may interfere with the count, and thus provide an unsatisfactory calibration. A suitable surfactant, for this purpose is Triton X-100 (Trade Mark of Rohm & Haas), a non-ionic detergent based on an octoxynol.

The dispersions of the invention are shelf-stable and remain functional for a period of at least one year.

The dispersions may optionally contain a white coloring agent, such as caseinate to simulate the appearance of milk.

The dye-bearing microbeads may be manufactured by procedures such as those described in U.S. Pat. Nos. 4,609,689; 4,714,682 and 5,073,493, the teachings of which are incorporated herein by reference.

iii) Suspending Agent

The aqueous dispersion of dye-bearing microbeads contains a suspending agent, the purpose of which is to maintain the microbeads in a dispersed or suspended state in the dispersion, and to prevent settling of the microbeads.

The dispersion may more properly be considered a colloid in that it comprises solid particles in a liquid dispersing medium, and is thus a suspension or dispersion.

The suspending agent is in particular a substance which increases the viscosity of the aqueous dispersion medium. Suitable suspending agents are polysaccharides having gelling characteristics. An especially suitable polysaccharide is carrageenin; the polysaccharide is employed in an amount below that at which gelling occurs, or in other words is in an amount below the gelling point, while being in an amount effective to increase the viscosity of the dispersing phase to a region in which the microbeads are non-settling or suspended in the dispersing phase. Typically the polysaccharide will be present in an amount of 0.01 to 0.5%, preferably about 0.05%, by weight, of the dispersion.

In the absence of the suspending agent, in accordance with the invention, low, inaccurate count readings are obtained.

iv) Electrolyte

The electrolyte should be present in the aqueous dispersion in an amount to provide an electrical conductivity which is substantially the same as, or greater that of milk. This electrical conductivity is necessary because of the mode of action of the counter machines being calibrated. The electrical conductivity is necessary to initiate a signal to the machine to operate.

Suitably the electrolyte will be present in a dissolved concentration of at least 100 mM, preferably at least 150 mM. Higher concentrations of electrolyte do not present any disadvantage but are not necessary. It is, however, preferred that the electrolyte only be present in solution so that amounts in excess of that which will dissolve in the aqueous dispersion should be avoided. In other words, the electrolyte should be present in an amount which dissolves in the aqueous dispersing medium, without precipitation.

Suitably electrolytes are the water soluble alkali and alkaline earth metal halides, for example, NaCl, KCl, $MgCl_2$ and $CaCl_2$.

b) Measurement of Somatic Cell Count

The Fossomatic machines are available in different capacities, including the Fossomatic 250 and Fossomatic 360, in which the last number refers to the sample counting capability per hour. The principle behind all Fossomatic counters is the same; they use opto-fluorescence to detect somatic cells. This method counts the number of cells per $\mu l$ of milk sample, which count is then multiplied by 1000 to give a cell count per ml of milk.

A Fossomatic is an automatic somatic cell counter used frequently by the dairy industry as a regulatory and indicator system to detect the presence of somatic cells in milk. The Fossomatic has an advantage over other methods in that it is easy to use and provides rapid results. It is usually referred to as an automatic fluorescence microscope because the detection of somatic cells relies on the reaction between the dye ethidium bromide and the DNA present in the nucleus of the somatic cell. When the ethidium bromide interacts with the DNA it produces a strong fluorescence. This dye has broad excitation bands which are centered around 280 nm and 460 nm and shows an emission wavelength around 600 nm. The fluorescence emission per unit cell is then detected and transformed into electrical pulses which are counted.

There are four basic solutions used in the analysis of somatic cells by the Fossomatic counter; the milk sample itself, buffer solution, dye solution and a rinsing liquid. The milk sample should be fairly fresh between 4–10 days old is adequate. It can either be fresh or preserved and preheated to 40° C. prior to the analysis to homogenize the fat into solution since up to 50% of the cells can be found in the fat layer. A sample volume of 0.2 ml of milk is used in the analysis.

The buffer solution is made up of potassium hydrogenphthalate, potassium hydroxide and 1% Triton x-100 solution in deionized water. The volume of buffer solution used for each sample is 1.8 ml. The dye solution is 0.2%, by weight, ethidium bromide. The total dye volume used for each sample is 2 ml. The rinsing liquid is used to remove all trace of the previous sample and typically consists of 10 ml of 1% Triton and 24 ml of 25% ammonia solution in 10 liters of deionized water.

The milk sample within a 40 ml container is preheated to 40° C. and is placed in the sampling position in which it is first stirred then a volume of 0.2 ml of milk is removed and thoroughly mixed with 1.8 ml of the buffer and 2 ml of the dye solution. The temperature of these liquids is maintained between 60° and 65° C. Since the total volume of this mixture is 4 ml, the dilution factor is 20. A microsyringe then transfers this mixture to a constant speed rotating disc. The disc is in a vertical position and is 100 mm in diameter, has a width of 2 mm. Twenty $\mu$l of liquid is laid out as a 0.5 mm wide and 10 $\mu$m thick film on the rotating disc to form a continuous film.

The disc rotates under a microscope and cells are magnified and illuminated by light from a high pressure 75 W Xenon arc lamp filtered by an excitation filter passing only blue light. Red fluorescent light emitted from the cells due to excitation of ethidium bromide/DNA complex passes through an emission filter than a 150 $\mu$m slit width to a photomultiplier. Each fluorescing cell produces a small emmitance signal which is converted to an electrical pulse. The total number of pulses is recorded after each sample has been analyzed and is multiplied by 1000 to give corrected values.

c) Calibration

Prior to the present invention there is no standard calibration sample which is shelf stable and reproducible. In Canada, calibration milk samples are prepared by Guelph Central Milk Testing Laboratory. These samples are prepared by collecting somatic cells found at the bottom of bulk milk tanks. These somatic cells are resuspended and serial dilutions are made in preserved milk. The number of somatic cells present is verified using a direct microscopic method. The Dairy Herd Analysis Service (PATLQ Inc.) located at the Macdonald Campus of McGill University, Quebec, uses such samples to calibrate the Fossomatic instruments with three standards consisting of 100,000 cells/ml, 400,000 cells/ml and 900,000 cell/ml. Although the range at which the Fossomatic can count is broad, between 1,000 to 10,000,000 cells/ml, the maximum number of cells counted as typically found in milk samples is 1,000,000 cells/ml.

The aqueous dispersion of the invention is produced with a predetermined number of microbeads/ml and thus may be produced with a microbead count of 100,000/ml, 400,000/ml or 900,000/ml corresponding to the prior standards conventionally employed.

The calibration standards of the invention are suitably produced in a form to fit physically within the commercially available counting machines; in particular they are packaged in 40 ml plastic vials for the Fossomatic and Bentley machines.

The counter machines are calibrated by utilizing the calibration standard of predetermined characteristic in the machine, in place of the milk sample as described in b) above and evaluating the electrical pulses based on the known microbead content of the dispersion to provide the relationship between the electrical pulses and the number of beads. This relationship provides the calibration by which the unknown number of somatic cells in the milk sample can be determined from the electrical pulses recorded when using the milk sample in the machine.

BRIEF DESCRIPTION OF THE DRAWINGS

The invention is illustrated by reference to the accompanying drawings in which.

DESCRIPTION OF PREFERRED EMBODIMENT WITH REFERENCE TO DRAWINGS

Figure 1:
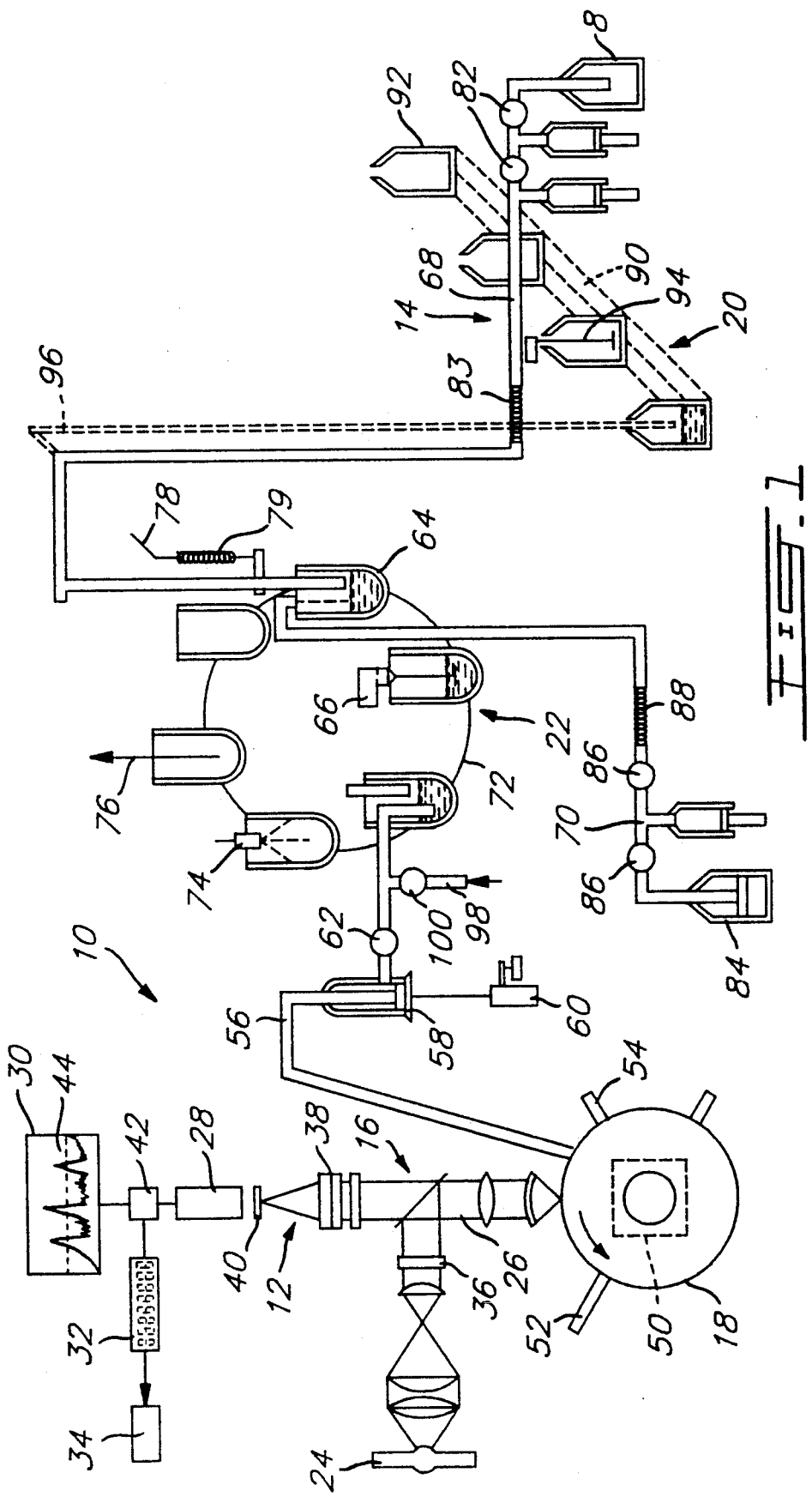
FIG. 1 illustrates schematically an apparatus for optical somatic cell counting of the Fossomatic type, in which the aqueous dispersion of the invention can be employed for calibration purposes.

With further reference to FIG. 1, there is illustrated schematically a commercial cell counter assembly of the Fossomatic (Trade Mark) type.

Cell counter assembly 10 includes a cell counter 12 and a sample feed line 14.

Cell counter 12 includes an optical counter 16, a rotating table 18, a sampling station 20 and sample preparation station 22.

Optical counter 16 includes a Xenon arc lamp 24, a microscope 26, a photomultiplier 28, an oscilloscope 30, a counter 32 and printer 34.

An excitation filter 36 is disposed between Xenon arc lamp 24 and microscope 26, and an emission filter 38 is disposed between microscope 26 and a slit 40.

A preamplifier 42 is disposed between photomultiplier 28 and oscilloscope 30 and counter 32.

Oscilloscope 30 includes a discriminator 44.

Rotating table 18 is driven by motor 50 and has a source of water in the form of water inlet 52 and a source of air in the form of air inlet 54.

Sample applicator 56 applies sample to rotating table 18.

Sample applicator 56 includes a mixer 58 driven by a motor 60, and a microsyringe 62.

Sample station 20 comprises a sample holder 64 which moves along a cyclic path 72.

The cyclic path includes a stirrer 66, a rinser 74, a suction dryer 76, a water feed line 78, a buffer feed line 68 and a dye feed line 70.

Water feed line 78 includes a heater 79.

Buffer feed line 68 includes buffer vessel 80, valves 82 and a heater 83.

Dye feed line 70 includes a dye vessel 84, valves 86 and heater 88.

Sample preparation station 22 includes a belt 90 carrying vessel 92 with milk to be sampled. Station 22 further includes a stirrer 94 and a sampling line 96.

Microsyringe 62 includes a water inlet 98 having a valve 100.

In operation, fresh or preserved milk samples in vessel 92 are conveyed on belt 90.

Prior to sampling, the milk in vessel 92 is stirred by stirrer 94, and thereafter a sample of known volume is withdrawn from the vessel 92 through sampling line 96 and delivered to sample holder 64.

The required amount of buffer solution is fed through buffer feed line 68 to sample holder 64, together with the required amount of dye through dye feed line 70 and water through water feed line 78.

The buffer solution, dye solution and water are heated to a temperature of 40° to 50° C. by their respective heaters 83, 88 and 79.

The milk sample under investigation in sample holder 64, together with the added buffer solution, dye and water is fed along cyclic path 72 to stirrer 66 where the sample is stirred to provide thorough mixing. Sample holder 64 continues along cyclic path 72 and a known portion is removed under pressure by microsyringe 62 mixed by mixer 58 and applied through sample applicator 56 to rotating table 18 to form a thin film which is viewed by microscope 26 as the thin film on rotating table 18 passes therebefore.

The cell-dye complex in the film is excited by filtered blue light (400-570 nm) from the Xenon arc lamp 24, and emits red fluorescence and the filtered fluorescence (590-700 nm) over a background removed by discriminator 44 is sensed by photomultiplier 28. The pulses resulting are transformed, counted by counter 32 and the results displayed on printer 34.

In the above-described system the dye is ethidium bromide.

The sample holder 64 which has moved downstream from microsyringe 62 is rinsed by rinser 74 and dried by suction dryer 76 and continues to the initial position for introduction of a fresh sample for investigation. The rotating table 18 is washed with water from water inlet 52 and dried with air from air inlet 54.

The cell counter assembly 10 is employed to counter the somatic cells in milk samples. The calibration is conducted employing the calibration standard of the invention which is applied to the rotating table 18 through sample applicator 56 via microsyringe 62. It will be understood that the calibration standard is pre-prepared with a predetermined number of microbeads per unit volume so that the sample preparation described for the milk sample is not carried out for the calibration.

EXAMPLE 1

Preparation of Calibration Standard

A master stock was prepared by mixing at 25° C. to 27° C., 975 ml of distilled (17.4 M $\Omega$) water, 0.5 g carrageenin, 11.7 g sodium chloride and 1 ml of Fluoresbrite polychromatic (from Polysciences Inc., Warrington, Pa., U.S.A.), having a bead content of $1 \times 10^6$ beads/ml.

The bead count of the master stock was counted on 8 samples with a hemocytometer and the average count was taken as the actual. In making the count a film of the master stock having a thickness or depth of 0.1 mm is spread on a surface divided into squares 1 mm $\times$ 1 mm and the bead count on 8 of the squares is recorded and the average determined.

Since the hemocytometer could not distinguish between single beads and aggregates of two or more beads adhered together additional beads are added to the master stock based on the observed statistical occurrence of double beads in the Fluoresbrite polychromatic. This correction is achieved by adding 72% more beads to the master stock.

Calibration standards are produced by appropriate dilution, a diluent containing 17.4 M $\Omega$ distilled water to achieve a desired bead count, the dilution being carried out with mixing.

Thus from the master stock containing a bead concentration equivalent for optical counting to $1 \times 10^6$ beads/ml, the following bead concentrations were achieved by dilution:

| Bead Conc. in beads/ml | Master stock ml | Diluent ml |
| --- | --- | --- |
| $5 \times 10^5$ | 10 | 10 |
| $4 \times 10^5$ | 8 | 12 |
| $2 \times 10^5$ | 4 | 16 |

The diluent comprises the distilled water containing the carrageenin and sodium chloride.

We claim:

1. A shelf-stable milk calibration standard of non-milk origin comprising an aqueous dispersion of microbeads bearing a fluorescent dye, a suspending agent effective to maintain said microbeads in a dispersed state in said dispersion and an electrolyte in an amount to provide the dispersion with an electrical conductivity which is substantially at least that of milk said dye having an excitation wavelength below 580 nm and having a fluorescence emission wavelength in the range of 550 to 660 nm, with said excitation wavelength being at least 10 nm below said emission wavelength, and said microbeads being present in a predetermined number per unit volume of the dispersion.

2. A standard according to claim 1, wherein said dispersion further contains a buffer effective to establish a pH of 6 to 8.

3. A standard according to claim 1, wherein said microbeads are of polystyrene and said dye has a fluorescence emission wavelength above 590 nm, said microbeads having diameters in the range of 0.5 to 10 microns.

4. A standard according to claim 3, containing $5 \times 10^4$ to $1 \times 10^6$ beads/ml of dispersion.

5. A standard according to claim 4, wherein said suspending agent is a polysaccharide present in an amount below the gelling point in the dispersion, effective to suspend said microbeads in the dispersion.

6. A standard according to claim 5, wherein said polysaccharide is carrageenin in an amount of 0.01 to 0.5%, by weight, of said dispersion.

7. A standard according to claim 6, wherein said electrolyte is present in an amount of at least 100 mM, which amount dissolves in said dispersion, without precipitation.

8. In a method of determining the somatic cell count of milk in which a sample of the milk is mixed with a dye which reacts with the somatic cells to produce fluorescence, and the fluorescence is detected and transformed to electrical pulses which are counted and evaluated based on a calibration standard of predetermined characteristics, the improvement wherein said calibration standard is as defined in claim 1.

* * * * *